(12) United States Patent
Haar

(10) Patent No.: US 8,280,642 B2
(45) Date of Patent: Oct. 2, 2012

(54) ANALYSIS SYSTEM FOR DETERMINING AN ANALYTE IN A BODY FLUID

(75) Inventor: Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 965 days.

(21) Appl. No.: 12/233,889

(22) Filed: Sep. 19, 2008

(65) Prior Publication Data

US 2009/0082973 A1 Mar. 26, 2009

(30) Foreign Application Priority Data

Sep. 22, 2007 (EP) .................................. 07018674

(51) Int. Cl.
*G01N 33/48* (2006.01)
*G06F 11/00* (2006.01)

(52) U.S. Cl. ........... 702/19; 702/188; 702/189; 702/190

(58) Field of Classification Search ............... 702/19, 702/30–32, 117–126, 187–190
See application file for complete search history.

(56) References Cited

U.S. PATENT DOCUMENTS

| | | | |
|---|---|---|---|
| 4,775,237 A * | 10/1988 | Cioppi | 356/417 |
| 5,676,143 A | 10/1997 | Simonsen et al. | |
| 6,055,060 A * | 4/2000 | Bolduan et al. | 356/433 |
| 6,955,060 B2 | 10/2005 | Homan et al. | |
| 2002/0016535 A1 | 2/2002 | Martin et al. | |
| 2003/0153820 A1 * | 8/2003 | Berner et al. | 600/345 |
| 2005/0023137 A1 | 2/2005 | Bhullar et al. | |
| 2006/0156796 A1 | 7/2006 | Burke et al. | |
| 2007/0173761 A1 | 7/2007 | Kanderian et al. | |

FOREIGN PATENT DOCUMENTS

| | | |
|---|---|---|
| EP | 0 735 363 B1 | 7/2005 |
| EP | 1 702 561 A2 | 9/2006 |
| GB | 2 024 432 A | 1/1980 |
| WO | WO 01/67099 A1 | 9/2001 |

OTHER PUBLICATIONS

Joseph S. Alford, Bioprocess Control: Advances and Challenges, Computers & Chemical Engineering, 2006, p. 1464-1475, vol. 30, Elsevier Ltd.

* cited by examiner

*Primary Examiner* — Phuong Huynh
(74) *Attorney, Agent, or Firm* — Krieg DeVault LLP

(57) ABSTRACT

An analysis system for determining an analyte of a body fluid comprises a test element and an analysis instrument having a measurement and evaluation unit. The test element has a sample application zone and two analysis zones and a reagent system, whose reaction with the analyte results in a detectable change characteristic for the desired analytical result. The measurement and evaluation unit comprises two analog measuring units, in each of which an analog measurement signal corresponding to one of the analysis zones is generated, two analog-digital converters for digitizing the analog measurement signal, a comparator unit for comparing control data values based on the digitized measurement signals, and a final processing unit, in which, if the determined deviation between the control data values of the digitized measurement signals is less than a predefined value, at least one of the control data values is allowed to pass for further processing into the desired analytical result.

18 Claims, 5 Drawing Sheets

ANALYSIS SYSTEM FOR DETERMINING AN ANALYTE IN A BODY FLUID

CROSS-REFERENCE TO RELATED APPLICATIONS

Applicants claim foreign priority benefits under Title 35 U.S.C. §119 of European Patent Application No. EP 07018674.7 filed on 22 Sep. 2007, which is incorporated herein by reference in its entirety.

FIELD OF THE INVENTION

The present invention relates to an analysis system for determining an analyte in a body fluid, comprising a test element having a reagent system, whose reaction with the analyte results in a detectable change characteristic for the desired analytical result, and an analysis instrument with a measuring and evaluation unit.

BACKGROUND

Analysis systems for determining an analyte in a body fluid which use disposable test elements, test carriers, or test strips are known in the prior art. Systems of this type are used for determining the concentration of various analytes. For example, the glucose content or the cholesterol content in blood is determined.

The test elements typically contain a reagent system made of one or more reagents whose reaction with the sample liquid results in a detectable change which can be measured using the analysis system. In photometrically operating analysis systems, a color change occurs in a detection layer in the test element as a reaction of the test element with the sample, which can be photometrically measured using a measurement and evaluation unit belonging to the analysis system. For example, the intensity of the light reflected by the test element is determined.

Alternatively, so-called electrochemical analysis systems are also used, in which the dispensing of a liquid sample onto the test element results in an electrochemical reaction which is detected as a detectable charge change, current flow, or voltage change.

The known analysis systems typically operate reliably when used properly. Nonetheless, erroneous measurement results can occur as a result of application errors with the analysis instrument or the test element. Although great care is taken in the production of such analysis systems and test elements, high quality control is desirable, during which malfunctions of the measuring device are determined to avoid erroneous results.

In particular for glucose measurement systems, in which the glucose content in the blood is determined, a high quality and a low error tolerance are required. The results of the concentration determination of the glucose content in the blood are the basis for the therapy of a patient. The dosing of the insulin is determined on the basis of the determined glucose content, so that an error-free analysis value is very important. A treatment of patients which is based on an erroneous measurement result and therefore results in an incorrect dosage of insulin (too low or too high insulin dose), can result in body-threatening and life-threatening situations.

For this reason, redundant systems are used, in which, for example, two photometric detectors connected in parallel are positioned, which determine the light reflected from an analysis zone. A system of this type is described in U.S. Pat. No. 6,955,060. Alternatively, two separate analysis zones can be illuminated using two light sources to determine two different analysis results using one detector.

Error influences of analysis systems can generally have an effect on a mechanical, measurement technology, or electronic level. The digital subsystems themselves can be monitored well, but in digital-analog partial systems, a quality control to ensure measurement precision and/or correctness is significantly more difficult.

To increase the measurement precision and avoid errors in particular, multiple measurements independent from one another can be performed by a patient. For example, a user can perform two independent measurements in sequence using the same device but two different test elements. However, it is not reasonable to expect a procedure of this type for the user in practical use.

Alternatively, to increase the measurement reliability, a measurement can be performed using two devices completely independent from one another. This also results in a significantly increased measurement and cost outlay, which is not practical.

It is therefore the object of the present invention to improve the known analysis systems in such a manner that the reliability is increased.

SUMMARY

According to one aspect, the analysis system for determining an analyte in a body fluid comprises a test element having a reagent system whose reaction with the analyte results in a detectable change which is characteristic for the desired analytical result. The test element has a sample application zone and two analysis zones. The analysis system comprises an analysis instrument having a measurement and evaluation unit. The unit contains (at least) two analog measuring units, in each of which an analog measurement signal corresponding to the change in one of the analysis zones is generated, two analog-digital converters for digitizing the analog measurement signal, a comparator unit for comparing control data values which are based on the digitized measurement signals, and a final processing unit. If the determined deviation between the compared control data values of the digitized measurement signals is less than a predefined value, at least one of the control data values is enabled in the final processing unit and the enabled control data value(s) is/are processed further into the desired analytical result.

In the meaning of the present invention, the term "corresponding" analog measurement signal is to be understood in such a manner that the value of the measurement signal is a measure of the change in the analysis zone. The measurement signal can be proportional to the change, which is not to be understood in the strictly mathematical sense, but rather also comprises the typically nonlinear relationships between an analyte concentration and a measurement signal.

In the context of the invention it has been determined that it is especially important to design the overall evaluation channels, which comprise the analysis zones, the analog measuring unit, and the analog-digital converter, redundantly, because error influences can occur both on the mechanical level or measurement technology level, and also on the electronic level, for example, in the form of so-called bit flips. While embodiments are known in the prior art which monitor the digital components of an analysis system, for example, through checking by software algorithms, the monitoring of combined digital-analog systems or partial systems encounters great difficulties. This is solved by the redundant configuration of the measurement channels. Alternatively, not only two evaluation channels, but rather also more than two redundant evaluation channels can be implemented.

According to another aspect, the analysis system is constructed redundantly in such a manner that two independent measurements are performed in parallel to one another. Each of the two analysis zones is assigned to an analog measuring unit and an analog-digital converter, so that an analog measurement signal is generated in the analog measuring unit which is proportional to the change in the analysis zone and/or is a measure of the change. A digital unit comprising the analog-digital converter digitizes the measurement signal from the analog measuring unit. The analysis system thus comprises two evaluation channels operating independently from one another, which comprise not only the analog measuring unit, but rather also the digital unit implemented as the analog-digital converter. Both measurements are thus performed completely independently of one another and can be performed in parallel and simultaneously. The analysis system delivers very secure and reliable results. Because the user does not notice the parallel measurements, the user friendliness of the system is very high. Measurement errors which can occur in one of the evaluation channels are recognized immediately. Analysis systems of this type are suitable in particular for glucose determination, because a very low error tolerance, a very high quality control, and secured analysis results are required.

A requirement for this purpose is the use of two different analysis zones. The term analysis zone is to be understood that it can comprise not only an area, but rather also an analysis volume and/or an evaluation volume, which means that the analysis zone can be three-dimensional. The two analysis zones thus can have the same size, but do not have to be volumes which spatially correspond to one another. Overlaps of the two analysis zones and/or a partial volume or a partial quantity, which both zones share, are entirely possible. The two analysis zones do not have to be identical, however, because otherwise the quality of the secured measurement results would be reduced.

To further increase the measurement precision and the avoidance of incorrect measurements, the analysis system according to another aspect can also be combined with additional measures such as the intrinsic monitoring of the analysis zones, for example, by wetting monitoring or impedance measurements. However, errors of this type are also recognized by the analysis system according to the invention.

The analysis system has the further advantage that it can be integrated in other devices. For example, the analysis system according to the invention can be integrated in a combined piercing and analysis system in which a wound is produced in a body part and blood and/or a body fluid is received from this wound and transported into the system. The body fluid must only be transported by the piercing system to the analysis zones of the analysis system, in which a measurable change is caused by the reaction with the body fluid.

According to the invention, digital control data values, which are each based on the digitized measurement signals, are compared to one another in the comparator unit. These control data values represent the measurement signals which were determined on the basis of the detected change in the analysis zone. In any case, a control data value is a "processing value" or "intermediate value" which is determined (e.g., calculated) from the digitized measured value of the measurement signal. These intermediate values can also be raw data. In this case, they are identical with the digitized measurement signals. The control data value is thus a value generated in the processing chain between the digitization of the analog measurement signal and the desired analytical result. The control data value can also be an determined concentration value of the analyte.

The analytical result is the value which is produced by further processing of at least one control data value. It is outputted to the user or transmitted to a further instrument, for example. The analytical result can alternatively be based on two concentration values which are determined from the digitized measurement signals. The concentration values can also be based on the control data values, which are in turn produced from the digitized measurement signals.

Before further processing of the control data values into the desired analytical result is performed, at least one of the control data values must be enabled by the final processing unit. This is performed if the deviation between the control data values determined in the comparator unit is less than a predefined limit which is referred to as threshold value.

Both measurements in the evaluation channels are only free of errors if the two evaluation channels provide equal (or identical) control data values or their deviation is less than the prescribed limit (tolerance value). As soon as an error occurs in one of the evaluation channels, whether due to an error in the analog measuring unit, in the analog-digital converter, or, for example, due to incomplete wetting of one of the analysis zones, this error is recognized immediately because of an excessive deviation of the two control data values. The processing to produce an analytical result is then terminated or repeated. It is thus ensured that a faulty result is not outputted. An error signal can additionally be generated and outputted.

The analysis system is suitable for the optical detection of the change caused in the reagent system, such as a color change, and also for an electrochemical evaluation, in that a current flow and/or a voltage change is detected. The optical measurements can comprise fluorescence measurements, luminescence measurements, or similar measurements in this case. Measurements of a light signal generated by diffuse reflection or measurements which are based on the principle of transmission are typical.

A simple embodiment of an optical analysis system (based on an optical detection) can comprise a measurement and evaluation unit into which a constant light signal is emitted and in whose analog measuring unit a change of the received measurement signal is measured. In a more complex embodiment, modulated or pulsed light signals are generated. The analog measuring unit is implemented in such a manner that the received measurement signal is accordingly assigned chronologically, to obtain signals from the "background" (noise), for example.

If electrochemical analysis systems are used (having an electrochemical detection of the change), in a simple embodiment of the measurement and evaluation unit, a polarization voltage can be applied to the analysis zones and a current caused by the chemical reaction can be measured in the analog measuring unit. However, different AC voltages can also be applied in chronological sequence to obtain further information from the determination of the impedance in addition to the current measurement. Obtaining additional information is described, for example, in US 2006/0156796.

The (summary) term "analog measurement signal" used in the context of this invention therefore relates to the part of the analysis system in which analog signals are generated and also measured. The analog measurement signals can therefore also comprise complex time curves depending on the embodiment of the analysis system.

Independently of the type of the measurement (optical measurement or electrochemical measurement), the two analysis channels can either be identical or can be constructed at least partially symmetrical. During an optical measurement, only one optical transmitter is preferably used for emitting light onto the (two) analysis zones. The measurement and evaluation unit preferably comprises two optical receivers. Each receiver is assigned to an analysis zone in such a manner that the optical receiver receives the light reflected from the analysis zone. The optical receivers can be photocells or photodiodes or similar receivers, for example. In a preferred embodiment, each of the two analog measuring units generates an analog measurement signal which is proportional to the reflected light received by the particular optical receiver, wherein the received light is reflected from the particular analysis zone.

If the two measurement channels are constructed identically, the analysis instrument comprises two optical transmitters, each sender emitting light onto one of the two analysis zones. The two optical senders are advantageously activated or supplied by one signal generator.

In a preferred embodiment, the data control values are desired concentration values. Two concentration values are then supplied to the comparator unit for comparison. The predefined value as a permissible limit for the deviation of the concentration values is a reference concentration value. In this preferred embodiment, a desired concentration value is already generated from the digitized measurement signal, which is then processed further in the comparator unit and the final processing unit if the deviation of the two concentration values is less than the reference concentration value.

BRIEF DESCRIPTION OF THE FIGURES

The invention is explained in greater detail hereafter on the basis of preferred embodiments shown in the figures. The special features shown therein can be used individually or in combination to provide preferred embodiments of the invention. In the figures.

DETAILED DESCRIPTION OF THE ILLUSTRATED EMBODIMENTS

Figure 1:
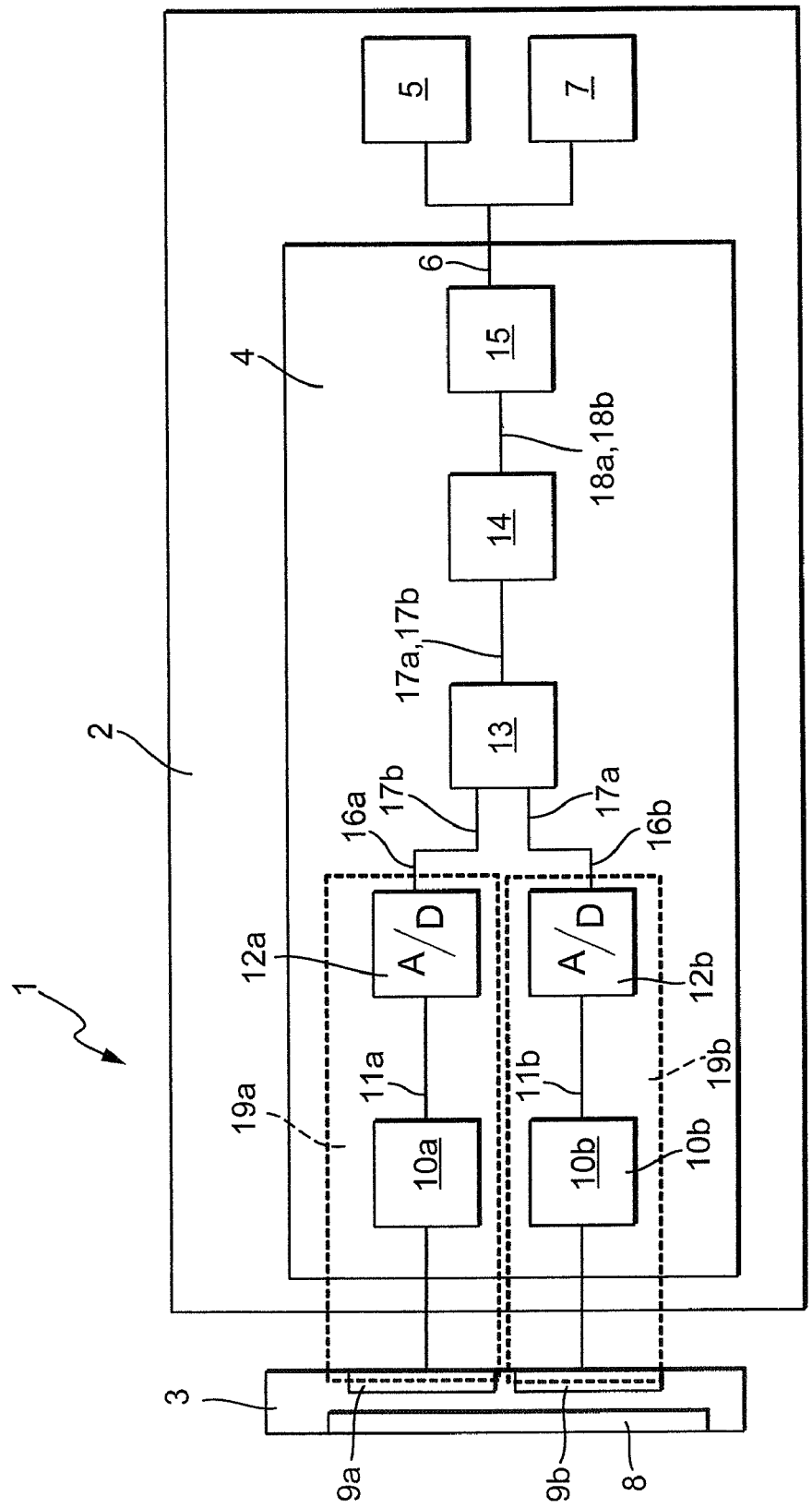
FIG. 1 shows a schematic block diagram of an analysis system according to the invention.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIGS. 1 through 4 show an analysis system 1 according to the invention having an analysis instrument 2 and a test element 3. The analysis instrument 2 has a measurement and evaluation unit 4 and preferably an output unit 5, to which the analytical result 6 determined by the measurement and evaluation unit 4 or an error signal is outputted.

The output unit 5 can display the analytical result 6 as an optical signal, for example, as a numeric value, e.g., a glucose value, or in the form of various symbols. In addition, an acoustic output of the results is also possible. The output unit 5 can provide further information in addition to the analytical result 6, for example, a successful measurement can be outputted in clear text or as a signal tone, as can an error signal. In addition, additional information can be displayed for the user.

The analysis instrument 2 as shown in FIGS. 1 through 4 optionally comprises a memory 7, in which measurement results are stored, for example, intermediate values or analytical results 6. A history of the measurement results can be stored in this manner. The memory can be read out via an interface by a connected device or a computer, for example. The analytical results 6 or further information can, alternatively or additionally to the display at the output unit 5, also be transmitted to further devices via the interface to be processed further or archived.

The test element 3 has a sample application zone 8 and two analysis zones 9a, 9b. The sample application zone 8 is preferably positioned on a top side of the test element 3, and the analysis zones 9a, 9b are positioned on the bottom side of the test element. In a preferred embodiment, the test element 3 has a capillary channel between the sample application zone 8 and the two analysis zones 9a, 9b. A body fluid, which is applied to the sample application zone 8, is conducted to the analysis zones 9a, 9b by means of the capillary channel. The capillary channel is not shown in FIGS. 1 through 4.

Both the sample application zone 8 and also the analysis zones 9a, 9b and the capillary channel can be part of the reagent system of the test element 3, in that upon a reaction of a body fluid within an analyte, a detectable change characteristic for the analyte is caused, which can be detected on the analysis zones 9a, 9b. As shown in the Figures, the two analysis zones 9a, 9b are different from one another, an overlapping area being possible. Both analysis zones 9a, 9b therefore have different analysis volumes, which means they have different volumetric dimensions.

The change of the reagent system of the test element 3 detectable in the analysis zones 9a, 9b is detected by two analog measuring units 10a, 10b, in each of which an analog measurement signal 11a or 11b is generated, which is proportional to the change in the particular analysis zone 9a or 9b, respectively.

The measurement and evaluation unit 4 comprises two analog-digital converters 12a, 12b (A/D converters) whose input is connected to the output of the particular analog measuring unit 10a, 10b and to whose input the analog measurement signal 11a or 11b is applied.

In the exemplary embodiment according to FIG. 1, the measurement and evaluation unit 3 comprises a comparator unit 13, an evaluation unit 14, and a final processing unit 15, which are connected in series in the processing chain.

The analog signals 11a or 11b applied to the input of the A/D converters 12a, 12b are digitized and transmitted from the A/D converters 12a, 12b as digitized measurement signals 16a, 16b to the comparator unit 13 in the form of digital control data values 17a, 17b. In the embodiment according to FIG. 1 the control data values 17a, 17b are identical to the digitized measurement signals 16a, 16b. The control data values 17a, 17b are compared to one another in the comparator unit 13 and transmitted to the evaluation unit 14. The desired concentration values 18a, 18b are determined from the control data values 17a, 17b using an analysis algorithm in the evaluation unit 14. The evaluation algorithm comprises an assignment between control data values 17a, 17b and concentration values 18a, 18b. This assignment can be stored in the form of a table in the evaluation unit 14, for example.

If the deviation between the control data values 17a, 17b determined in the comparator unit 13 is less than a predefined value (threshold value), in the final processing unit 15 at least one of the control data values 17a, 17b and/or the concentration values 18a, 18b based on the control data values 17a, 17b is enabled (allowed to pass). The enabled control data values 17a, 17b or concentration values 18a, 18b are processed further in the final processing unit 15 into the analytical result 6, which is available for further processing at the output of the measurement and evaluation unit 4.

Both control data values 17a, 17b are preferably allowed to pass (enabled) by the final processing unit 15 if the deviation between the two control data values 17a, 17b is less than the predefined value. They are then preferably processed further into the desired analytical result 6 on the basis of both control data values 17a, 17b. The analytical result 6 is especially preferably calculated from the mean value of the two control data values 17a, 17b. In the final processing unit 15, the arithmetic mean or the geometric mean can be calculated from the two values. Other mean value calculations, such as a weighted mean value, are also possible. The analytical result 6 can preferably also be the mean value of the two concentration values 18a, 18b.

Alternatively, the analytical result 6 can either be determined from the lower or the higher of the two control data values 17a, 17b in the final processing unit 15. Instead of the control data values 17a, 17b, the concentration values 18a, 18b can also be used here.

If the determined deviation between the control data values 17a, 17b is more than the predefined value, preferably no allowance to pass occurs in the final processing unit 15. An error signal is generated instead, which is transmitted to the output unit 5.

In the embodiment according to FIG. 1, the analysis system 1 has two redundantly designed evaluation channels 19a, 19b, which each comprise an analysis zone 9a, 9b, an analog measuring unit 10a, 10b, and an A/D converter 12a, 12b.

Figure 2:
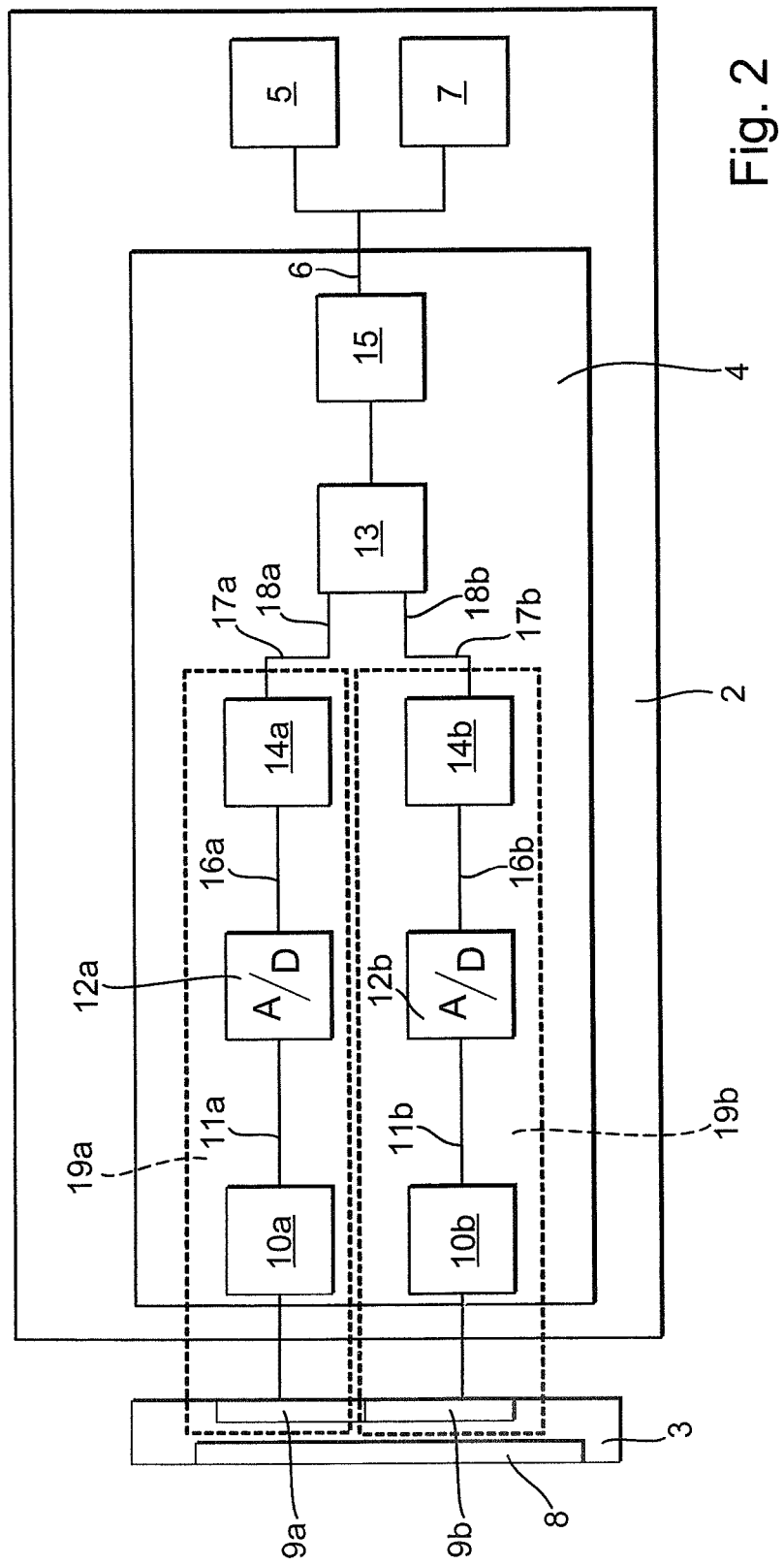
FIG. 2 shows a schematic block diagram of a further embodiment of an analysis system.

The embodiment according to FIG. 2 also has two redundant evaluation channels 19a, 19b. These evaluation channels 19a, 19b each comprise an evaluation unit 14a, 14b in addition to the analysis zone 9a, 9b, the analog measuring unit 10a, 10b, and the A/D converter 12a, 12b. The measuring and evaluation unit 4 preferably thus has two evaluation units 14a, 14b. A control data value 17a, 17b is generated in each of the evaluation units 14a, 14b from the digitized measurement signal 16a, 16b using an evaluation algorithm. The evaluation algorithm comprises an assignment between values of the digitized measurement signal 16a, 16b and the control data values 17a, 17b.

The control data values 17a, 17b are preferably the concentration values 18a, 18b. In this preferred case, the evaluation algorithm comprises an assignment between values of the digitized measurement signal 16a, 16b and concentration values 18a, 18b, so that concentration values 18a, 18b which correspond to the detected change in the analysis zones 9a, 9b are outputted in the evaluation units 14a, 14b. Two concentration values 18a, 18b are compared to one another in the comparator unit 13.

The assignment of the evaluation algorithm of the evaluation units 14, 14a, 14b is preferably determined by a calibration. During the calibration, a digital reference measurement signal is generated for each reference concentration value. Then the signals and values are stored in the form of a table or the like, for example, in a memory, such as a RAM, an EPROM, an EEPROM, or the like, for example. A nonvolatile memory is preferably used, which can be integrated in one of the digital components, such as the evaluation unit 14, 14a, 14b, for example.

By determining the concentration values through calibration beforehand, on one hand a very simple and rapid conversion of the digitized measured values into concentration values can be performed. On the other hand, batch-specific assignments can also be stored in the devices, so that different assignments between the detected changes of the analysis zones of the test elements and the concentration values can be implemented as a function of the test elements used (such as test strips or similar objects).

Because the digital evaluation unit 14a, 14b is implemented redundantly, errors (such as sporadic errors, bit flips), which occur under specific operating conditions or environmental conditions and which are not systematically recognizable, are recognized in the evaluation unit 14a, 14b. The reliability of the analysis system 1 according to the invention is increased once again by the coverage of errors of this type.

The analytical result 6 is determined from the concentration values 18a, 18b compared to one another in the final processing unit 15, which, as explained above, is determined from both or one of the concentration values 18a, 18b after allowance to pass by the final processing unit 15.

Figure 3:
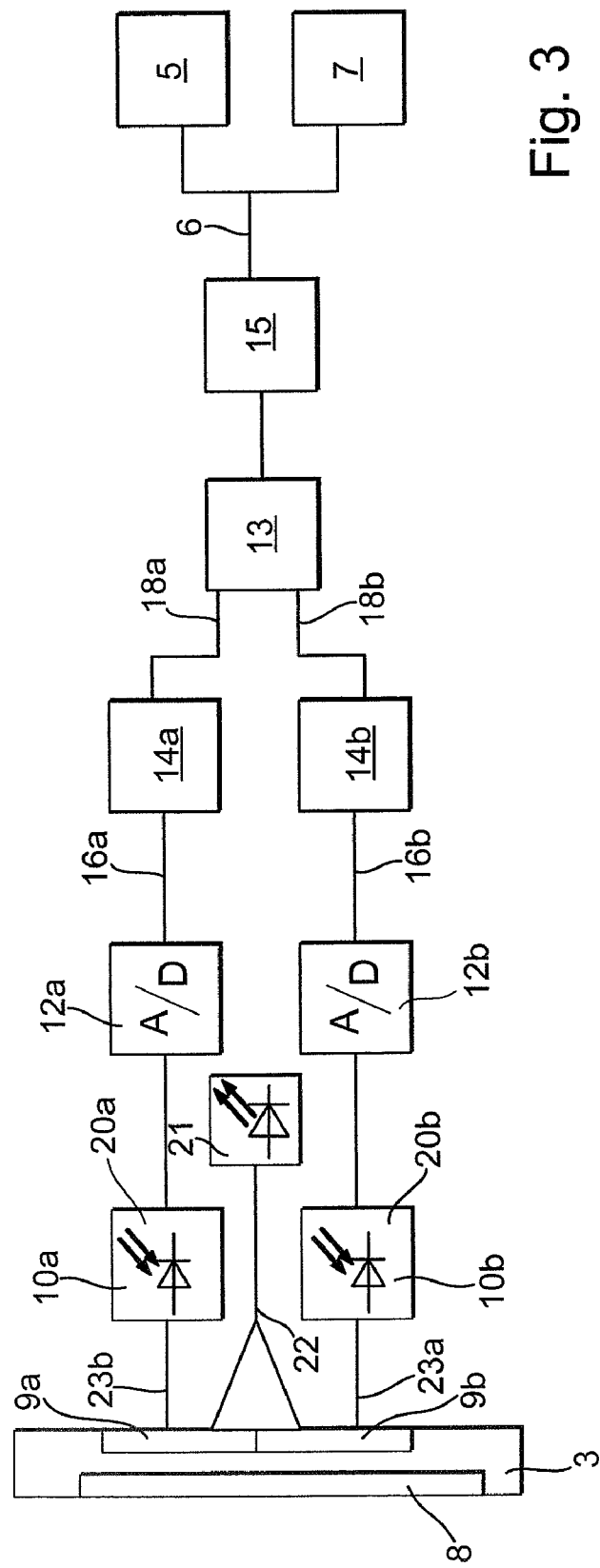
FIG. 3 shows the block diagram of an analysis system according to FIG. 2 based on an optical measurement.

FIG. 3 shows an embodiment of the analysis system 1 according to the invention in which the two evaluation channels 19a, 19b also comprise the (redundant) evaluation units 14a, 14b. In this preferred embodiment, the measurement and evaluation unit 4 comprises two optical receivers 20a, 20b for receiving reflected light from each of the analysis zones 9a, 9b. The optical receiver 20a receives reflected light from the analysis zone 9a; the optical receiver 20b receives reflected light from the analysis zone 9b. The optical receivers 20a, 20b are integrated in the analog measuring units 10a, 10b. The analysis instrument 2 has an optical transmitter 21 for emitting light onto the two analysis zones 9a, 9b of the test element 3. The emitted light is reflected on the analysis zones 9a, 9b and received by the two analog measuring units 10a, 10b which contain the optical receivers 20a or 20b, respectively. Each analog measuring unit 10a, 10b generates an analog measurement signal 11a, 11b, which is proportional to the reflected light of the corresponding analysis zone 9a, 9b.

Especially preferably, as shown in FIG. 3, an optical fiber 22 is positioned between the optical transmitter 21 and the analysis zones 9a, 9b, using which at least one of the analysis zones 9a, 9b is irradiated with light. Both analysis zones 9a, 9b are especially preferably illuminated with light, so that a reflection of the light occurs on the particular analysis zone 9a, 9b. An optical fiber 23a, 23b is preferably positioned between each optical receiver 20a, 20b and the assigned analysis zone 9a, 9b, to transmit the light reflected from the corresponding analysis zone 9a, 9b to the optical receiver 20a, 20b.

The analog measurement signals 11a, 11b generated from the optical light signals are then processed further in the known way as in the embodiment according to FIG. 2 until an analytical result 6 has been determined. In this embodiment, as in the other embodiments, the control data value 17a, 17b and/or the concentration values 18a, 18b are preferably only allowed to pass if the determined deviation between the control data values 17a, 17b and/or the concentration values 18a, 18b lies below a predefined limit. Otherwise, the allowance is prevented and an error signal is generated which can be outputted at the output unit 5.

In an alternative embodiment of an analysis system 1 which is based on an optical measurement, two optical transmitters can also be provided, by each of which one analysis zone 9a, 9b is irradiated with light. The two evaluation channels 19a, 19b then each comprise one of the two optical transmitters, so that both channels are designed identically.

An analysis system based on an optical measurement has the advantage that a very rapid and simple measurement of the change in the analysis zones 9a, 9b can be performed. This contactless measurement has the advantage that a spatial separation of the test element 3 and the analysis instrument 2 can occur. In particular if optical fibers are used, such as optical waveguides made of polymer or glass fiber or the like, optical measurement offers a large amount of design configurations, in particular upon the integration into existing combined piercing and analysis systems.

Figure 4:
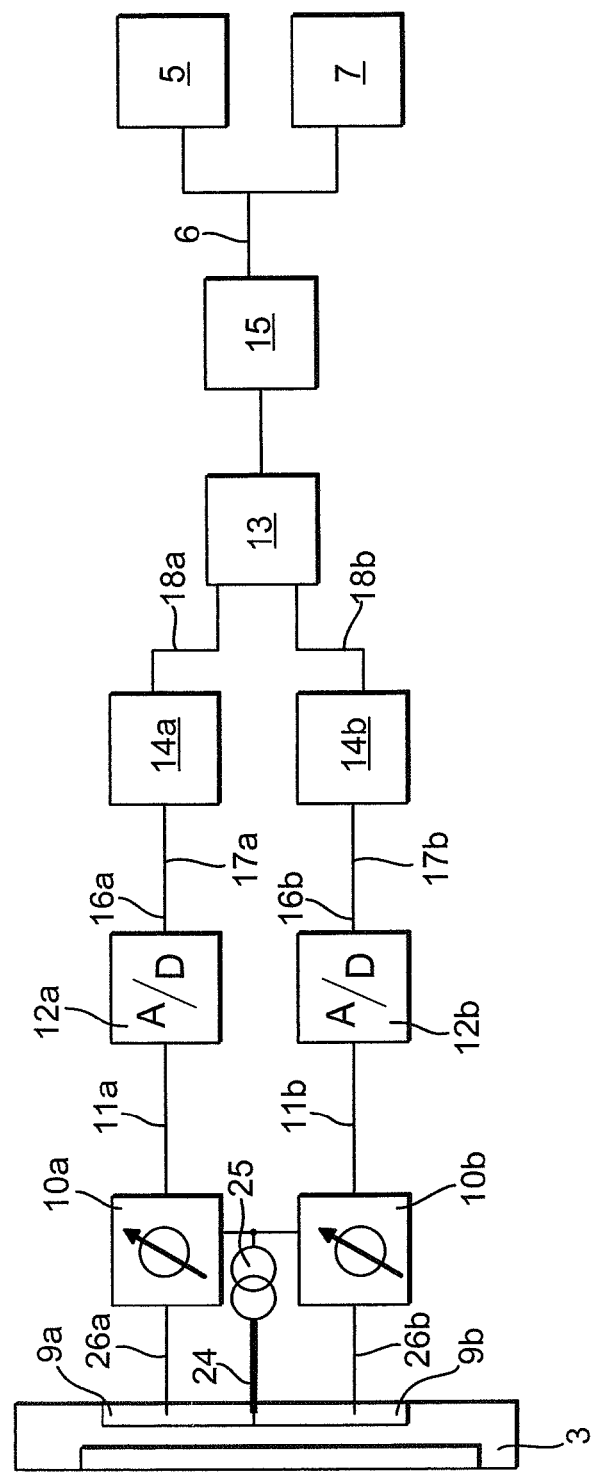
FIG. 4 shows the block diagram of an analysis system according to FIG. 2 based on an electrochemical measurement.

FIG. 4 shows a further preferred embodiment of the analysis system according to the invention according to FIG. 2, whose measurement principle is based on an electrochemical measurement. An electrical conductor 24 connects an electrical source 25, which can be a voltage source or current source, to the two analysis zones 9a and 9b. Two electrical conductors 26a, 26b contact the particular analysis zones 9a, 9b with the associated analog measuring units 10a, 10b in such a manner that a current flow through the conductor 24, the analysis zones 9a, 9b, and the electrical conductors 26a, 26b (as the return) is measurable in the analog measuring unit 10a or 10b. Of course, the measurement and evaluation unit 4 can comprise the components known in the prior art, so that in addition to a polarization voltage, different AC voltages can also be generated in chronological sequence in the electrical source 25. In addition to a current measurement, the impedance can additionally be determined, from which further information about the sample liquid can be obtained.

Alternatively, two separate circuits can also be constructed, in that two electrical sources are provided which each contact one of the analysis zones 9a, 9b using one electrical conductor.

Figure 5:
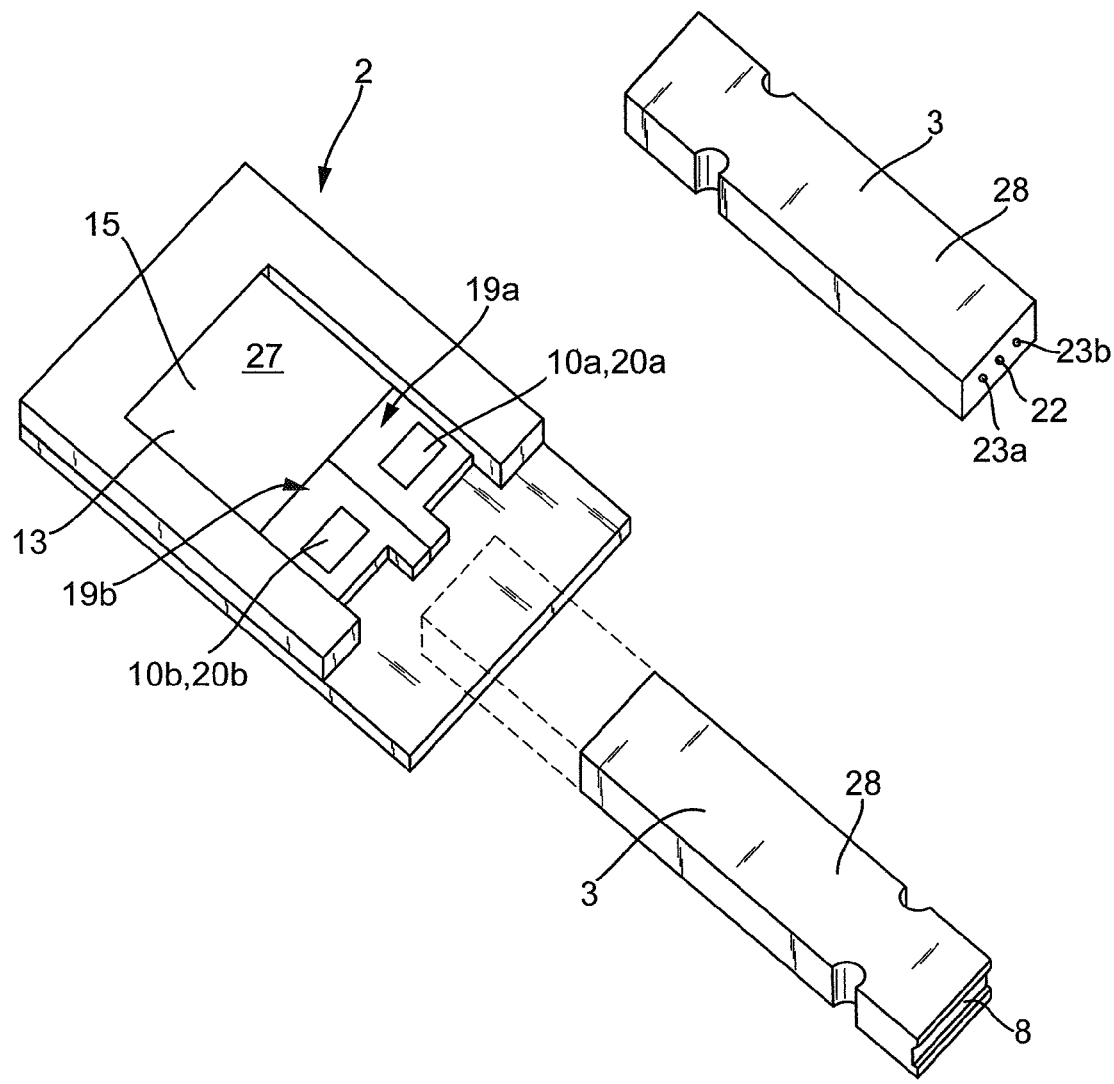
FIG. 5 shows a schematic circuit diagram of an analysis instrument and a test element implemented in the form of a stick.

FIG. 5 shows a preferred embodiment of an analysis instrument 2 having two identically constructed evaluation channels 19a, 19b which are connected to an electronic unit 27. The electronic unit 27 comprises the comparator unit 13 and the final processing unit 15. The analysis instrument 2 uses an optical measuring principle, so that the analog measuring units 10a, 10b each comprise an optical receiver 20a, 20b.

The test element 3 is implemented as a test stick 28. The sample application zone 8 is positioned on one of the narrow sides of the test element 3. Three optical fibers run in parallel in the test stick 28, the middle optical fiber 22 transmitting light from the analysis instrument 2 to the analysis zones 9a, 9b (not visible here), which are positioned below the sample application zone 8. The two outside optical fibers 23a, 23b transmit the light reflected from the analysis zones 9a, 9b back to the optical receivers 20a, 20b of the analysis instrument 2.

The implementation of the test element 3 as a test stick 28 has the advantage that a test stick of this type can be handled very well and meets high acceptance with the user. A clear separation of sample application zone 8 and the measurement and evaluation unit 4 is concurrently implemented. Nonetheless, the test stick 28 operates with very small quantities of blood in the range of 100 nl or less, because the analysis zones 9a, 9b and the sample application zone 8 are implemented as very compact and small. The transmission pathways of the liquid are very short. Due to the optical transmission using light, the actual measurement technology can be integrated in the instrument 2 remotely from the sample application zone 8.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary. Furthermore, all patents, patent applications, and publications cited herein are hereby incorporated by reference.

The invention claimed is:

1. An analysis system for determining an analyte in a body fluid, comprising:
   a test element with a reagent system, whose reaction with the analyte results in a detectable change which is characteristic for the desired analytical result, with a sample application zone and with two analysis zones, and
   an analysis instrument with a measurement and evaluation unit, which comprises:
   two analog measuring units, in each of which an analog measurement signal corresponding to one of the analysis zones is generated,
   two analog-digital converters for digitizing the analog measurement signal,
   a comparator unit for comparing control data values based on the digitized measurement signals, and
   a final processing unit, in which, if a determined deviation between the control data values of the digitized measurement signals is less than a predefined value, at least one of the control data values is allowed to pass for further processing into the desired analytical result.

2. The analysis system according to claim 1, wherein the control data values are concentration values and the predefined value is a reference concentration value.

3. The analysis system according to claim 2, wherein the measurement and evaluation unit comprises an evaluation unit in which concentration values are determined from the control data values using an evaluation algorithm and the evaluation algorithm comprises an assignment between the control data values and concentration values, the evaluation unit being positioned between the comparator unit and the final processing unit.

4. The analysis system according to claim 3, wherein the assignment of the evaluation algorithm is performed by a calibration wherein digitized reference measurement signals are generated for reference concentration values.

5. The analysis system according to claim 2, wherein the measurement and evaluation unit comprises two evaluation units in which concentration values are determined from the digitized measurement signals each using an evaluation algorithm, which comprises an assignment between values of the digitized measured signals and concentration values, the evaluation units being positioned in the processing chain before the comparator unit.

6. The analysis system according to claim 5, wherein the assignment of the evaluation algorithm is performed by a calibration wherein digitized reference measurement signals are generated for reference concentration values.

7. The analysis system of claim 1, wherein:
the analysis instrument has an optical transmitter for emitting light onto the analysis zones, and
the measurement and evaluation unit has two optical receivers each for receiving light from one analysis zone, and
an analog measurement signal is generated in each of the two analog measuring units, which analog signals are proportional to the light reflected from each of the analysis zones.

8. The analysis system of claim 7, wherein an optical fiber is positioned between the optical transmitter and an analysis zone and configured so that at least one of the analysis zones is irradiated with light, and an optical fiber is positioned between each optical receiver and each analysis zone and configured so that reflected light from the analysis zone is transmitted to the optical receivers.

9. The analysis system according to claim 1, wherein the measurement and evaluation unit comprises a first electrical conductor which is contacted with at least one of the analysis zones, and a second electrical conductor, which is contacted with an analysis zone and an analog measuring unit and configured so that a current flow through the first electrical conductor, the at least one analysis zone, and the second electrical conductor is measurable by the one analog measuring unit.

10. The analysis system according to claim 1, wherein a capillary channel is positioned between the sample application zone and the analysis zones, whereby the body fluid is transferred onto the analysis zones.

11. The analysis system according to claim 1, wherein the two analysis zones have analysis volumes different from one another.

12. The analysis system according to claim 1, wherein if the deviation between two control data values in less than the predefined value, both control data values are enabled in the final processing unit and the further processing into the desired analytical result is performed on the basis of both control data values.

13. The analysis system according to claim 12, wherein the analytical result is determined from the mean value of the two control data values.

14. The analysis system according to claim 1, wherein if the deviation between two control data values in less than the predefined value, only one of the control data values are enabled in the final processing unit and the further processing into the desired analytical result is performed on the basis of the lower or higher of the two control data values.

15. The analysis system according to claim 1, wherein if the determined deviation between the control data values of the digitized measurement signals is more than the predefined value, the control data values are not allowed to pass and an error signal is generated.

16. The analysis system according to claim 1, wherein the analysis instrument comprises an output unit, at which the analytical result or an error signal is outputted.

17. The system according to claim 1, wherein the measurement signals from each of the two analog measuring units are digitized by a corresponding one of the two analog-digital converters for digitizing the analog measurement signal in parallel to one another.

18. The system according to claim 17, wherein the measurement signals from each of the two analog measuring units are digitized simultaneously by the two analog-digital converters.

* * * * *